United States Patent [19]

Baggiolini et al.

[11] 4,247,704
[45] Jan. 27, 1981

[54] HEXAHYDRO THIENO IMADAZOLE INTERMEDIATES FOR THE SYNTHESIS OF BIOTIN

[75] Inventors: Enrico G. Baggiolini, Bloomfield; Hsi L. Lee, West Paterson; Milan R. Uskokovic, Upper Montclair, all of N.J.

[73] Assignee: Hoffmann-La Roche Inc., Nutley, N.J.

[21] Appl. No.: 43,282

[22] Filed: May 29, 1979

Related U.S. Application Data

[63] Continuation-in-part of Ser. No. 965,660, Dec. 1, 1978, which is a continuation-in-part of Ser. No. 822,119, Aug. 5, 1977, Pat. No. 4,130,713.

[51] Int. Cl.³ .................................................. C07D 495/04
[52] U.S. Cl. ..................................................... 548/303
[58] Field of Search ......................................... 548/303

[56] References Cited

U.S. PATENT DOCUMENTS

| 2,489,235 | 11/1949 | Goldberg et al. | 548/303 |
| 2,489,236 | 11/1949 | Goldberg et al. | 548/303 |
| 2,489,237 | 11/1949 | Goldberg et al. | 548/303 |
| 3,533,915 | 10/1970 | Hanka et al. | 548/303 |
| 3,687,967 | 8/1972 | Field et al. | 548/303 |
| 3,740,416 | 6/1973 | Gerecke et al. | 548/303 |
| 3,957,794 | 5/1976 | Baggiolini et al. | 348/303 |
| 3,983,134 | 9/1976 | Matsui et al. | 548/303 |
| 4,014,895 | 3/1977 | Aoki et al. | 548/303 |

FOREIGN PATENT DOCUMENTS

| 46-3580 | 1/1971 | Japan | 548/303 |
| 51/8289 | 1/1976 | Japan | 548/303 |

OTHER PUBLICATIONS

Baker et al. "J. Org. Chem." vol. 12, pp. 167–173 (1946).
Harris et al. "Science" vol. 97, pp. 447–448 (1943).

Primary Examiner—Henry R. Jiles
Assistant Examiner—Jane T. Fan
Attorney, Agent, or Firm—Jon S. Saxe; Bernard S. Leon; George W. Johnston

[57] ABSTRACT

A process is disclosed for producing d-biotin from L or DL-cystine ester via novel intermediates.

9 Claims, No Drawings

HEXAHYDRO THIENO IMADAZOLE INTERMEDIATES FOR THE SYNTHESIS OF BIOTIN

RELATED APPLICATIONS

This application is a continuation-in-part of U.S. patent application Ser. No. 965,660, filed Dec. 1, 1978, which in turn is a continuation-in-part application of U.S. patent application Ser. No. 822,119, filed Aug. 5, 1977, now U.S. Pat. No. 4,130,713.

BACKGROUND OF THE INVENTION

This invention relates to a process for preparing d-biotin.

Optically active d-biotin, also known as vitamin H, is a natural product found in kidneys, livers, egg yolks, milk and yeast. This compound is used medicinally to treat various dermatitis.

Biotin has been prepared synthetically by Harris et al. (Science, Vol. 97, pg. 447, 1943), Baker et al. (J. Org. Chem., Vol. 12, p. 167, 1947) as well as Goldberg et al. (U.S. Pat. Nos. 2,489,235 and 2,489,236). Many synthetic processes for the production of biotin followed these works. Some of the intermediates produced by the processes had more than one assymetric carbon atom, and a plurality of mixtures of isomeric intermediates resulted. Some of the isomers, however, could not be utilized to form optically active d-biotin. To obtain the desired enantiomer for producing d-diotin, the isomeric mixtures had to be separated into their components by costly and time consuming techniques which led to a decrease in the yield of the desired product.

SUMMARY OF THE INVENTION

We have invented a novel process for the synthesis of optically active d-biotin of the formula:

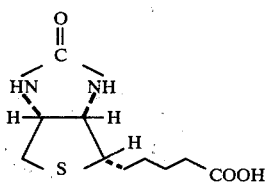

from cystine ester of the formula:

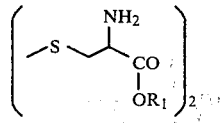

wherein $R_1$ is lower alkyl, aryl or aryl (lower) alkyl, or its racemate, via novel intermediates.

In accordance with the present invention, cystine ester is transformed through various intermediates to a nitrone of the formula:

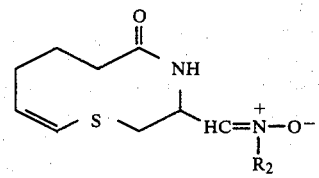

wherein $R_2$ is an aryl (lower) alkyl such as benzyl.

Nitrone VI is transformed to a tricyclic isoxazolidine of the formula:

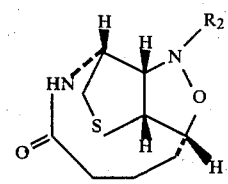

wherein $R_2$ is as above.

Isoxazolidine VII is transformed through various novel intermediates to a known compound of the formula:

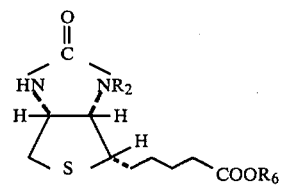

wherein $R_2$ is as above and $R_6$ is hydrogen, lower alkyl or aryl (lower) alkyl.

Compound XV ultimately is converted to d-biotin of formula I.

In a further aspect of the invention, optically active L-cystine ester can be transformed through the above compounds to d-biotin.

The process of the present invention advantageously avoids the formation of many undesirable intermediate isomers as it produces optically active d-biotin.

DETAILED DESCRIPTION

The present invention concerns a novel process for producing optically active d-biotin from L or DL-cystine ester via novel intermediates.

As used herein, alkyl connotes straight or branched chain saturated aliphatic hydrocarbon groups containing 1 to 20 carbon atoms. Lower alkyl means alkyl groups having from 1 to 7 carbon atoms (e.g., methyl, ethyl, n-propyl, isopropyl and hexyl). Lower alkoxy means alkoxy groups having from 1 to 7 carbon atoms (e.g., methoxy, ethoxy and isopropoxy). Lower alkylene denotes alkylene groups of 2–6 carbon atoms (e.g., ethylene, propylene and butylene). Lower alkanol connotes alkanols having 1–7 carbon atoms (e.g., methanol, propanol and hexanol). Lower alkylenedioxy denotes a moiety derived by the condensation of the hydroxy group of a 1,2 or 1,3 diol with a carbonyl function. The alkylene group of lower alkylenedioxy has 2 to 5 carbon atoms. Typical lower alkylenedioxy groups are ethylenedioxy, 1,2propylenedioxy, 2,4 butylenedioxy and 2,3 pentylenedioxy. Alkanoic acid connotes lower alkyl carboxylic acids such as acetic acid, isopropionic acid and hexanoic acid.

Aryl denotes mononuclear aromatic hydrocarbon groups such as phenyl and the like which can be unsubstituted or substituted in one or more positions with halogen, nitro lower alkylenedioxy, lower alkyl or lower alkoxy. Aryl also denotes polynuclear aryl groups such as napthyl, anthryl, phenanthryl, azulyl and the like which can be unsubstituted or substituted with one or more of the aforementioned substituents.

Arylakyl connotes a group comprising aryl and alkyl moieties as defined hereinbefore. Aryl (lower) alkyl defines a group comprising aryl and lower alkyl moieties as defined hereinbefore, particularly benzyl and α-lower alkyl substituted benzyls (e.g., cumyl). Halogen denotes chlorine, bromine and iodine. Alkali metals include lithium, sodium, potassium and rubidium. Alkaline earth metals include barium, magnesium, calcium and strontium.

In the pictorial representations of the compounds of this application, a solid tapering line ( ▶ ) indicates a substituent which is in the β-orientation (above the plane of the molecule) and a dashed line (- - -) indicates a substituent which is in the α-orientation (below the plane of the molecule).

In accordance with the present invention, d-biotin of the formula:

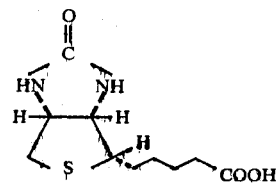

is produced from cystine ester of the formula:

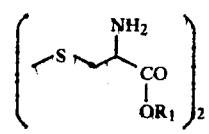

where $R_1$ is lower alkyl, aryl or aryl (lower) alkyl, by the reaction scheme shown hereinbelow. For illustration, the compounds of the formulas VII through XV and I are shown in their optically active configuration. The racemates of such optically active compounds are also intended.

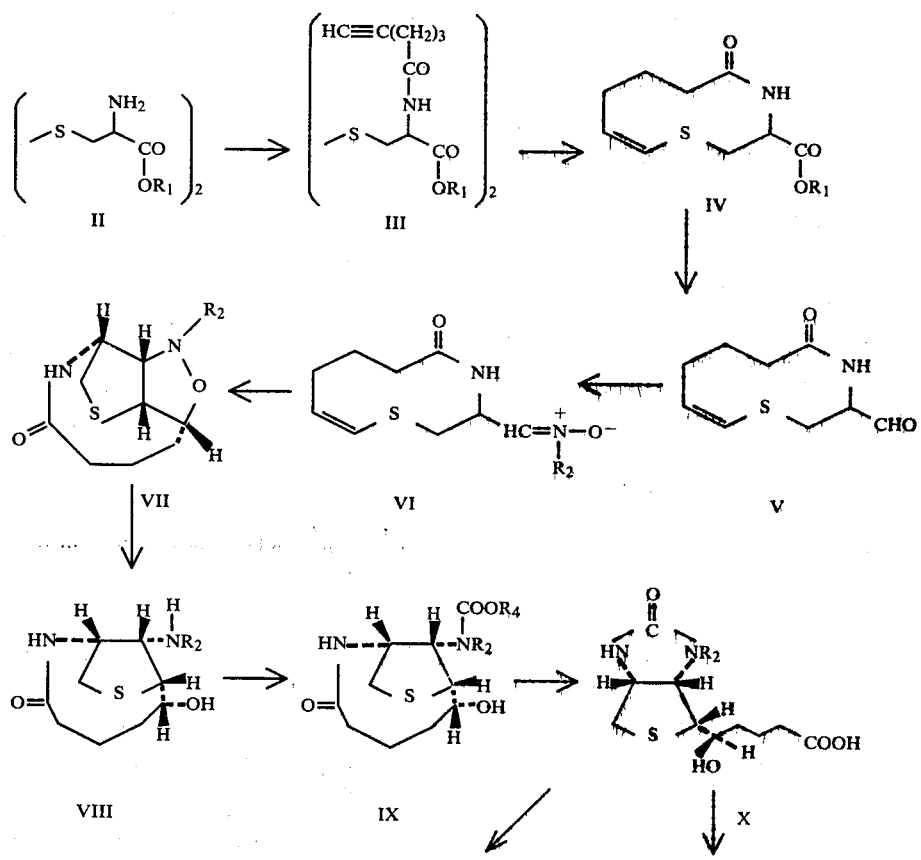

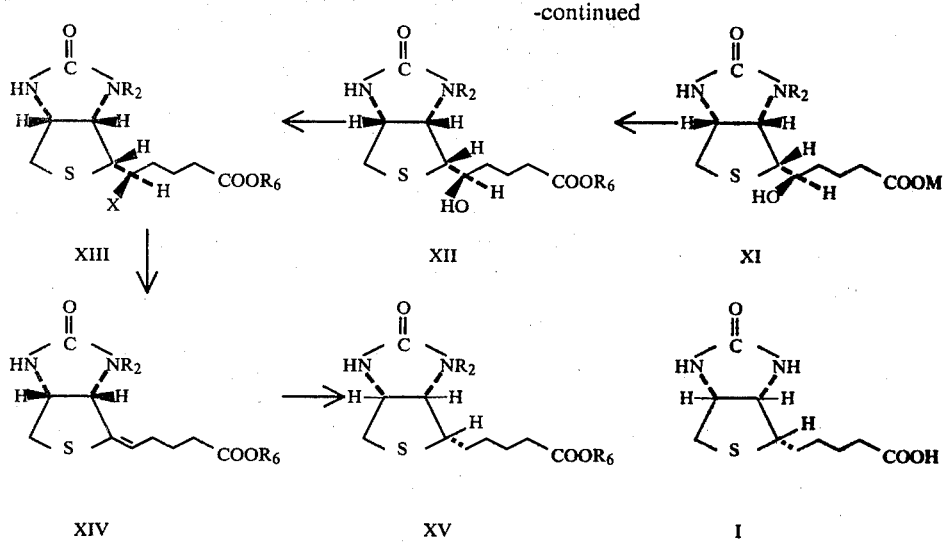

XIII  XII  XI

XIV  XV  I wherein $R_1$ and $R_4$ each are lower alkyl, aryl or aryl (lower) alkyl; $R_2$ is aryl (lower) alkyl, $R_6$ is hydrogen, lower alkyl or aryl (lower) alkyl; X is halide and M is alkali metal or alkaline earth metal.

The starting material for the above scheme is L-cystine ester of formula II or its racemate DL-cystine ester. Such starting materials are known or can be formed from known compounds by standard reactions.

L or DL-cystine ester II is acylated with 5-hexynoly halide in basic media to form an acetylenic amide of formula III. Typical 5-hexynoyl halides are 5-hexynoyl chloride and 5-hexynoyl bromide. The basic media may be inorganic or organic. Typical inorganic bases include alkali metal hydroxides, carbonates and bicarbonates (e.g., sodium hydroxide, sodium carbonate and potassium bicarbonate) and suitable organic bases include tertiary amines (e.g., pyridine and triethyl amine). Although not necessary, the reaction may proceed in an organic solvent (e.g., dioxane and tetrahydrofuran) or an aqueous mixture thereof (e.g., mixture of water and tetrahydrofuran). The temperature is not critical but the reaction is generally carried out between about $-30°$ and about 30° C. and preferably at 0° C.

Amide III is treated with zinc powder and a lower alkanoic acid (e.g., acetic acid) or an alkanoic acid-water mixture to form a vinyl sulfide olefinic ester of formula IV. By the above treatment, the disulfide bond of compound III is reduced with concomitant intramolecular cyclization to form the 10-membered ring olefinic ester IV. Although temperature is not critical, the reaction generally proceeds from about 10° to about 80° C., and room temperature (about 23° C.) is preferred.

If L-cystine ester II is utilized as the starting material, amide III and ester IV are produced in their optically active L-configuration. If DL-cystine ester II is utilized as the starting material, amide III and ester IV are produced as racemates.

Ester IV is reduced to an olefinic aldehyde of formula V via any conventional means for selectively reducing esters to aldehydes without affecting vinyl sulfide or lactam moieties. A preferred method includes treating ester IV with reducing agents such as diisobutylaluminum hydride and Li(t-butoxy)$_3$AlH. The reduction is conducted in the presence of an inert organic solvent (e.g., hexane, heptane, octane, toluene dioxane and tetrahydrofuran). The reaction is carried out at atmospheric pressure and at temperatures from about $-65°$ to about $-85°$ C. and preferably at about $-70°$ to about $-80°$ C.

If desired, aldehyde V in its racemic form can be resolved to produce the desired L-enantiomer by conventional means. Conventional means, such as reacting aldehyde V with an optically active hydrazine to form a diastereomeric hydrazone of aldehyde V, can be utilized. The optically active hydrazones are separated by known techniques such as crystallization. The particularly desired optically active aldehyde V can be regenerated from its optically active hydrazone by conventional methods well known in the art.

Aldehyde V is transformed to a nitrone of formula VI by treatment with an aryl (lower) alkyl hydroxylamine (e.g., benzyl hydroxylamine). The reaction proceeds in any inert organic solvent such as an ether (e.g., diethyl ether and tetrahydrofuran) or an aromatic hydrocarbon (e.g., benzene and toluene). Although temperature is not critical, the reaction proceeds generally between about 10° and about 50° C., and room temperature is preferred.

If optically active aldehyde V of the formula:

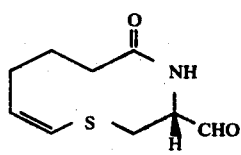

V-A is utilized to produce nitrone VI, the same optical configuration will be maintained throughout the reaction scheme. All of the intermediates VI–XV of the reaction scheme will be in their desired optically active form and d-biotin will result.

The compounds of formulas IV through VI can be collectively represented by the formula:

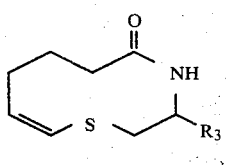

wherein R₃ is —COOR₁,

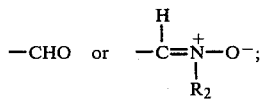

$R_1$ is lower alkyl, aryl or aryl (lower) alkyl and $R_2$ is aryl (lower) alkyl.

Nitrone VI is converted to a tricyclic isoxazolidine of formula VII by an intramolecular 1,3-dipolar addition of its nitrone moiety to its vinyl sulfide double bond. For this conversion, nitrone VI is heated from about 50° to about 200° C. in an inert organic solvent. A temperature range of about 80° to about 120° C. is preferred. In carrying out the conversion any conventional inert organic solvent can be utilized. Of course, the solvent must have a boiling point equal to or greater than the selected reaction temperature. Typical solvents include benzene, toluene, diglyme and xylene.

Alternatively, aldehyde V can be converted to isoxazolidine VII in one step by treatment with an aryl (lower) alkyl hydroxylamine as described above but at a temperature of between about 80° and about 150° C. The one step conversion of aldehyde V to isoxazolidine XII, however, increases the formation of unwanted byproducts.

When aldehyde V is converted to isoxazolidine VII (directly or via nitrone VI), isoxazolidine VII is produced either in its optically active form as set forth in the reaction scheme or as a racemic mixture of this optically active enantiomer and its corresponding enantiomer. If optically active aldehyde V-A is utilized to produce isoxazolidine VII (directly or via nitrone VI), compound VII is produced in the optically active configuration as set forth in the reaction scheme. If aldehyde V is utilized in its racemic form, isoxazolidine VII is produced as a racemic mixture of the optically active configuration depicted in the reaction scheme and its corresponding enantiomer.

Isoxazolidine VII is converted to a bicyclic amino alcohol of formula VIII by catalytic hydrogenation in a suitable solvent. Typical catalysts include platinum, palladium on charcoal and Raney nickel. Any organic solvent utilized in conventional catalytic hydrogenation may be employed. Suitable solvents include alcohols such as methanol, isopropanol and hexanol as well as alkanoic acids such as acetic acid. Although not critical, the temperature for the catalytic hydrogenation generally ranges from about 0° to about 50° C. Room temperature is preferred.

Alternatively, isoxazolidine VII is converted to amino alcohol VIII by treatment with zinc powder in a lower alkanoic acid (e.g., acetic acid) or in a lower alkanoic acid-water mixture. The temperature of the treatment is not critical and generally ranges from about 10° to about 80° C. Room temperature is preferred.

Amino alcohol VIII is acylated with a lower alkyl haloformate, aryl haloformate or aryl (lower) alkyl haloformate to form an urethane of formula IX. Typical haloformates include methyl chloroformate, phenyl bromoformate and benzyl chloroformate. The acetylation proceeds in basic media which may be inorganic or organic. Typical inorganic bases include alkali metal hydroxides, carbonates and bicarbonates (e.g., sodium hydroxide, sodium carbonate and potassium bicarbonate) and suitable organic bases include tertiary amines (e.g., pyridine and triethylamine). Although, not necessary, the reaction may proceed in an inert organic solvent (e.g., dioxane and tetrohydrofuran) or in an aqueous mixture thereof (e.g., mixture of water and tetrahydrofuran). The temperature is not critical but the reaction is generally carried out between about −30° and about 30° C. and preferably at 0° C.

The compounds of formulas VIII and IX can be collectively represented by the formula:

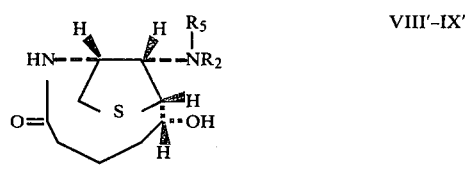

wherein $R_2$ is aryl (lower) alkyl, $R_5$ is hydrogen or —COOR₄ and $R_4$ is lower alkyl, aryl or aryl (lower) alkyl.

Urethane IX is converted to an imidazolidinone acid of formula X by treatment with a base. Suitable bases include alkali metal and alkaline earth metal hydroxides and alkoxides (e.g., sodium hydroxide, barium hydroxide and potassium alkoxide). The conversion proceeds in water or in a mixture of water and water miscible organic solvents. Typical solvents include dioxane, tetrahydrofuran, organic alcohols (e.g., methanol and isopropanol) and dimethylformamide. In the conversion of urethane IX to imidazolidinone acid X, temperature can range from about 50° to about 150° C. When barium hydroxide is utilized with a dioxane-water mixture, reflux temperature is preferred.

Imidazolidinone acid X is converted to an imidazolidinone ester of formula XIII via intermediates XI and XII. Imidazolidinone acid X is first converted to a metal salt of formula XI by any conventional method of converting an acid to its salt. A suitable technique includes neutralizing imidazolidinone acid X with an alkali metal hydroxide or alkoxide or alkaline earth metal hydroxide or alkoxide (e.g., sodium methoxide and barium hydroxide) to form metal salt XI. Temperature is not critical and can range from about 0° to about 50° C., and room temperature is preferred.

To produce intermediate XII, metal salt XI is treated with an alkyl halide or aryl (lower) alkyl halide (e.g., methylbromide and benzylchloride) in a solvent having a high dielectric constant. Suitable solvents include dimethyl formamide, hexamethyl phosphoramide and dimethyl sulfoxide. The formation of intermediate XII from metal salt XI proceeds at a temperature between about 10° and about 50° C., and preferably at room temperature.

Alternatively, imidazolidinone acid X is converted directly to intermediate compound XII without forming metal salt XI. More particularly, imidazolidinone acid X is reacted with a diazoalkane (e.g., diazomethane and diazoethane) in diethyl ether to form imidazolidinone XII. The reaction takes place preferably in an organic solvent (e.g., methanol, propanol and hexanol).

Although not critical, the reaction generally proceeds from about 0° to about 30° C. Room temperature is preferred.

Intermediate XII is reacted with a lower alkyl halosulfonate, aryl halosulfonate or aryl (lower) alkyl (e.g., methyl sulfonyl chloride, paratoluene sulfonyl bromide and benzyl sulfonyl chloride) in the presence of a tertiary amine such as pyridine and triethylamine to form a transient sulfonate. The transient compound reacts with the halogen ion present in the reaction mixture thereby forming imidazolidinone XIII. Although not necessary, the reaction is preferably carried out in an inert organic solvent such as an ether (e.g., diethyl ether and tetrahydrofuran) or an aromatic hydrocarbon (e.g., benzene and toluene). Although temperature is not critical, the reaction proceeds generally between about −20° and about 60° C. A temperature of about 0° C. is preferred.

The compounds X–XIII can be collectively represented by the formula:

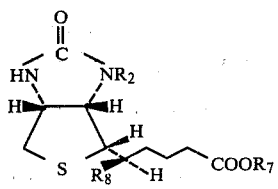

X'-XIII' wherein $R_2$ is aryl (lower) alkyl, $R_7$ is hydrogen, lower alkyl, aryl (lower) alkyl, alkali metal or alkaline earth metal; $R_8$ is is hydroxy or halide.

Imidazolidinone XIII can be converted to a compound of formula XIV by treatment with a strong non-nucleophilic organic base. Suitable bases include those alkali metal alkoxides and alkaline earth metal alkoxides which are non-nucleophilic (e.g., potassium tertiary butoxide and sodium tertiary butoxide). The reaction proceeds in a non-hydrolytic polar solvent such as dimethylsulfoxide and dimethylformamide. If desired, compound XIV, wherein $R_6$ is lower alkyl or aryl (lower) alkyl, can be worked up with water and saponified by conventional techniques to produce a compound of the same formula wherein $R_6$ is hydrogen.

Compound XIV can be converted to a known compound of formula XV via catalytic hydrogenation. Any conventional catalytic hydrogenation technique may be employed. Typical catalysts include palladium on charcoal, palladium on barium sulfate, platinum and Raney nickel. Any conventional solvent utilized in catalytic hydrogenation may be employed. Suitable solvents include organic alcohols (e.g., methanol, propanol and hexanol), acetic acid and water mixtures thereof. Although not critical, the temperature and pressure can range from about 5° to about 50° C. and from atmospheric pressure to about 500 psi. When palladium on charcoal is selected as the catalyst, room temperature and atmospheric pressure are preferred.

Compound XV is then treated with sodium in liquid ammonia or boiling hydrobromic acid to form biotin of formula I. When sodium in liquid ammonia is utilized, the treatment is carried out at atmospheric pressure and at temperatures varying from about −90° to about −40° C., and a temperature of about −70° C. is preferred. Although not necessary, the treatment can be carried out in an inert organic solvent such as tetrahydrofuran and dioxane or which act as cosolvents.

In accordance with the above procedures, cystine ester II is converted to biotin I. When DL-cystine ester is utilized as the starting material of the aforedisclosed procedures, the racemate of d-biotin results. As known in the art, racemic biotin then can be converted to optically active d-biotin of formula I by conventional resolution techniques and procedures. More particularly, racemic biotin is reacted with an optically active amine to form diastereomeric biotin salts which are separated by crystallization. Typically optically active amines include arginine, brucine, quinidine and dehydroabietylamine. The desired diastereomeric salt is placed in solution and after acidification and extraction, d-biotin of formula I is produced.

In accordance with a further aspect of the present invention, the racemate of aldehyde V can be separated into its optically active enantiomers by the aforedescribed techniques. Optically active enantiomer V-A can be converted to optically active d-biotin of formula I via optically active enantiomers of formulas VI through XV (shown in the previously described scheme) in accordance with the aforementioned procedures.

More particularly, optically active aldehyde V is transformed to optically active nitrone VI which is converted to optically active isoxazolidine VII, which in turn is converted to optically active amino alcohol VIII, which in turn, is acylated to optically active urethane IX, which in turn, is converted to optically active imidazolidinone acid X. The later compound is converted to optically active imidazolidinone ester XIII via optically active intermediates XI and XII. Optically active imidazolidinone XIII is converted to optically active compound XIV, which in turn, is catalytically hydrogenated to known optically active compound XV, which in turn, is converted to form optically active d-biotin I. Advantageously, such procedures avoid racemization of intermediates VI-XV or of the desired biotin end product.

In accordance with another aspect of the present invention, the racemates of formulas VII through XV can be converted into their optically active components by known techniques. The optically active component of these compounds (depicted in the aforementioned scheme) can then be converted to optically active d-biotin by the aforementioned procedures, without racemization.

Suitable techniques for converting racemates VII-XV into their optically actie components are described hereinbelow.

For example, racemic isoxazolidine VII is reacted with an optically active carboxylic acid or sulphonic acid to form diastereomeric salts of isoxazolidine VII. Typical optically active carboxylic acids include tartaric acid and camphoric acid. A suitable optically active sulphonic acid is d-camphor-10-sulphonic acid. The salts are separated by known techniques such as crystallization. The desired salt is placed in so. ition, basified and extracted to produce the optically active soxazolidine VII of the aforementioned scheme.

Racemic amino alcohol VIII can be reacted with an optically active carboxylic acid or sulphonic acid to form corresponding diastereomeric salts which are then separated by crystallization. Typical optically active acids include tartaric acid and d-camphor-10-sulphonic acid. Through known techniques, the desired enantiomer results.

Illustratively, racemic compounds IX, X and XII can be treated with optically active carboxylic acid chlorides or sulphonic acid chlorides to form corresponding diastereomeric esters. Typical optically active carboxylic acid chlorides include 3β-acetoxy-Δ[5]-etiocholenic acid chloride and menthomethoxyacetyl chloride. A suitable optically active sulphonic acid chloride is d-camphor-10-sulphonyl chloride. The esters can then be separated into their diastereomers by known techniques such as crystallization and chromatography.

Further, compounds X and XII through XV, wherein $R_6$ is hydrogen, is reacted with an optically active amine to form diastereomeric salts which are separated by crystallization. Typical optically active amines include arginine, brucine, quinidine and dehydroabietylamine. The desired salt is placed in solution, acidified and extracted to give the desired optically active compound.

The following Examples further illustrate the invention. All temperatures are in degrees Centigrade, unless otherwise stated. Ether connotes diethyl ether.

EXAMPLE 1 bis-5-Hexynamide-DL-cystine dimethylester

To a solution of 23.5 g. (87.6 mmol) of DL-cystine dimethylester and 16.6 g. (209.9 mmol) of pyridine in 300 ml. of dry dichloromethane, cooled at 0° C., a solution of 22.8 g. (174.6 mmol) of 5-hexynoyl chloride in 60 ml. of dry dichloromethane were added dropwise. After addition, the reaction mixture was stirred for 20 hours at 0° C., washed subsequently with 3×100 ml. of 1 N hydrochloric acid, 3×50 ml. of brine, 1×50 ml. of saturated sodium bicarbonate solution and 2×50 ml. of brine. Removal of the solvent gave 37.0 g. (92.5% yield) of crude bis-5-hexynamide-DL-cystine dimethylester. Crystallization from dichloromethane-n-hexane gave 36.0 g. (90% yield) of pure amide, mp 107°–108° C.

EXAMPLE 2

5-oxo-1-thia-4-aza-Cyclodec-9-ene-3-carboxylic acid methyl ester

To a solution of 5.0 g. (10.9 mmol) of bis-5-hexynamide-DL-cystine dimethylester in 600 ml. of glacial acetic acid, was added 25 g. (382.4 mmol) of zinc dust. The resulting suspension was stirred at room temperature for 100 hours. After filtration, the solvent was evaporated in vacuo. The residue was dissolved in 150 ml. of methylene chloride, washed with 2×50 ml. of 0.1 N hydrochloric acid, then with 3×50 ml. of 2 N sodium bicarbonate solution and finally washed with 3×50 ml. of brine. After drying, the solvent was removed to give 4.58 g. of crude 5-oxo-1-thia-4-azacyclodec-9-ene-3-carboxylic acid methyl ester. The product was purified by chromatography on a silica column, using methylene chloride-ethyl acetate (3:2 parts by volume) as eluent. The purified product, weighing 3.63 g. was crystallized from methylene chloride-ether to give 3.10 g. (62% yield) of pure 5-oxo-1-thia-4-azacyclodec-9-ene-3-carboxylic acid methyl ester, mp 160°–161° C.

EXAMPLE 3

5-oxo-1-thia-4-aza-Cyclodec-9-ene-3-carboxaldehyde

To a solution of 1.15 g. (5.02 mmol) of 5-oxo-1-thia-4-azacyclodec-9-ene-3-carboxylic acid methyl ester in 20 ml. of dichloromethane, cooled at −75° C., there was added dropwise 17 ml. (25.50 mmol) of a 1.5 m diisobutylaluminum hydride solution in toluene. The reaction mixture then was stirred at −75° C. for 25 minutes. Subsequently, 0.5 ml. of methanol were slowly added thereto. The solution was allowed to come to room temperature, diluted with 50 ml. of dichloromethane and washed with 3×30 ml. of 1 N hydrochloric acid. The combined aqueous layers were saturated with sodium chloride and extracted with 3×50 ml. of dichloromethane. The combined organic phases were washed with 3×50 ml. of brine, dried and evaporated to give 0.99 g. of 5-oxo-1-thia-4-azacyclodec-9-ene-3-carboxaldehyde as a white amorphous powder.

EXAMPLE 4

N-(5-oxo-1-thia-4-aza-Cyclodec-9-ene-3-methylene)-benzylamine N-oxide

A solution of 0.990 g. (4.97 mmol) of 5-oxo-1-thia-4-azacyclodec9-ene-3-carbaldehyde and 0.631 g. (5.00 mmol) of benzylhydroxylamine in 20 ml. of dry dichloromethane was stirred at room temperature overnight. The reaction mixture was concentrated to 10 ml. and the precipitate was filtered and washed with 50 ml. of etherhexane (1:1 parts by volume) to give 1.086 g. (72% yield) of N-(5-oxo-1-thia-4-azacyclodec-9-ene-3-methylene)benzylamine N-oxide as a white solid.

EXAMPLE 5 rac[1R-(1α,7α,8β,11β)]-9-Benzyl-10-oxa-12-thia-6,9-diazatricyclo[5,3,3,0$^{8,11}$]tridecan-5-one A mixture of 2.58 g. (8.48 mmol) of N-(5-oxo-1-thia-4-azacyclodec-9-ene-3-methylene)benzylamine N-oxide and 650 ml. of dry toluene was refluxed overnight. The solvent was removed and the residue was filtered through a small silica column, eluted with ethyl acetate to give 1.37 g. of rac[1R-(1α,7α,8β,11β)]-9-benzyl-10-oxa-12-thia-6,9-diazatricyclo[5,3,3,0$^{8,11}$] tridecan-5-one as a white powder. This product was purified on a 150 g. silica column, using ethyl acetate as eluent. The purified product was crystallized from acetone-ether. White crystals of rac[1R-(1α,7α,8β, 11β)]-9-benzyl-10-oxa-12-thia-6,9-diazatricyclo[5,3,3,0$^{8,11}$] tridecan-5-one were obtained (mp 161°–162° C.).

EXAMPLE 6 rac. [1R-(1α,7α,8α,11α)]-N-Benzyl-[7-hydroxy-3-oxo-9-thia-2-azabicyclo[6,2,1]undecan-11-yl]carbamic acid methyl ester A mixture of 0.190 g. (0.624 mmol) of rac.[1R-(1α,7α,8β,11β)]-9-benzyl-10-oxa-12-thia-6,9-diazatricyclo[5,3,3,0$^{8,11}$]tridecan-5-one, 20 ml. of 50% aqueous acetic acid and 0.6 g. of zinc dust was stirred at 70° C. for 4 hours. The reaction mixture was then filtered and evaporated in vacuo. The residue was treated with 25 ml. of a 2 N sodium carbonate solution and 12 ml. of tetrahydrofuran. Under continuous stirring, 0.210 g. (2.22 mmol) of methylchloroformate were added thereto and the resulting mixture was stirred at room temperature for 3 hours. The mixture was then extracted with ethyl acetate, the combined organic phases washed with brine, dried and the solvent was removed in vacuo. The residue was crystallized from methylene chloride-n-hexane mixture and recrystallized from methanol-ether to give 0.160 mg. (70% yield) of rac. [1R-(1α,7α,8α,11α)]-N-benzyl-[7-hydroxy-3-oxo-9-thia-2-azabicyclo[6,2,1]undecan-11-yl]carbamic acid methyl ester, mp 251°–252° C.

EXAMPLE 7 rac[3aS-(3aβ,4aα,4(R*),6aβ)]-Hexahydro-δ-hydroxy-2-oxo-3-(phenylmethyl)-1H-thieno[3,4-d]-imidazole-4-pentanoic acid methyl ester A mixture of 0.175 g. (0.480 mmol) of rac[1R,-(1α,-7α,8α,11α)]-[7-hydroxy-3-oxo-9-thia-2-azobicyclo[6,2,-1]undecan-11-yl]carbamic acid methyl ester, 0.35 g. of barium hydroxyde monohydrate, 20 ml. of water and 10 ml. of dioxane was refluxed under argon for 5 hrs. After cooling, the reaction mixture was acidified to pH 3 with 2 N hydrochloric acid and saturated with sodium chloride. The mixture was then extracted with ethyl acetate. The combined organic phases were washed with brine, dried and evaporated in vacuo. The residue was dissolved in 3 ml. of methanol and treated dropwise with a solution of diazomethane in ether, until persistence of the yellow color. Evaporation of the solvents in vacuo gave 0.168 g. of crude rac[3aS-(3aβ,4α,4(R*),6aβ)]-hexahydro-δ-hydroxy-2-oxo-3-(phenylmethyl)-1H-thieno-[3,4-d]-imidazole-4-pentanoic acid methyl ester.

This crude material was purified by chromatography to give 0.120 g. of pure product which gave white crystals from ether-acetone mixture, mp. 108°-109° C.

EXAMPLE 8 rac[3aS-(3aβ,4α,4(R*),6aβ)]-Hexahydro-δ-chloro-2-oxo-3-(phenylmethyl)-1H-thieno-[3,4-d]-imidazole-4-pentanoic acid methyl ester A mixture of 0.146 g. (0.421 mmol) of rac[3aS-(3aβ,-4α,4(R*),6aβ)]-hexahydro-δ-hydroxy-2-oxo-3-(phenylmethyl)-1H-thieno-[3,4-d]-imidazole-4-pentanoic acid methyl ester, 0.438 g. (3.82 mmol) of methanesulfonyl chloride and 5 ml. of dry pyridine was stirred at room temperature for 5 hours. After this time, it was diluted with 50 ml. of ethyl acetate, washed with 1 N hydrochloric acid and subsequently with water and brine, dried and evaporated in vacuo to give 0.160 g. of crude rac[3aS-(3aβ,4α,4(R*),6β)]-hexahydro-δ-chloro-2-oxo-3-(phenylmethyl)-1H-thieno-[3,4-d]-imidazole-4-pentanoic acid methyl ester. Crystallization from methylene chloride-ether gave 0.101 g. (63%) of pure product as white crystals, m.p. 141°-142° C.

EXAMPLE 9 rac[3aS-(3aβ,6aβ)]-Hexahydro-2-oxo-3-(phenylmethyl)-1H-thieno-[3,4-d]-imidazole-4-ylidene-pentanoic acid A mixture of 0.070 g. (0.183 mmol) of rac[3aS-(3aβ,-4α,4(R*), 6aβ)]-hexahydro-δ-chloro-2-oxo-3-(phenylmethyl)-1H-thieno[3,4-d]-imidazole-4-pentanoic acid methyl ester, 0.072 g. (0.64 mmol) of potassium tert.-butoxyde and 5 ml. of dry dimethyl sulfoxide was stirred under argon at 70° C. for 4 hrs. After cooling, 10 ml. of a 1 N sodium hydroxide was added and the resulting mixture extracted with ether. The aqueous phases were acidified with 1 N hydrochloric acid, saturated with sodium chloride and extracted with ethyl acetate. The combined ethyl acetate phases were washed with water, then with brine, dried and evaporated to give 0.060 g. of crude rac[3aS-(3aβ,6aβ)]-hexahydro-2-oxo-3-(phenylmethyl)-1H-thieno-[3,4-d]-imidazole-4-ylidene pentanoic acid.

EXAMPLE 10 rac[3aS-(3aβ,4β,6aβ)]-Hexahydro-2-oxo-3-(phenylmethyl)-1H-thieno-[3,4-d]-imidazole-4-pentanoic acid methyl ester A mixture of 0.59 g. (1.769 mmol) of rac[3aS-(3aβ,-6aβ)]-hexahydro-2-oxo-3-(phenylmethyl)-1H-thieno-[3,4-d]-imidazole-4-ylidene-pentanoic acid, 0.1 g. of 10% palladium on charcoal and 10 ml. of 50% aqueous acetic acid was hydrogenated at room temperature and under atmospheric pressure overnight. After filtering the catalyst, the filtrate was evaporated in vacuo. The residue was dissolved in 5 ml. of methanol and treated with a solution of diazomethane in ether, to persistence of the yellow color. The solvent was removed in vacuo. The residue was purified by chromatography (eluent: ethyl acetate-methanol 9:1 parts by volume) and crystallized from methylene chloride-ether to give 0.30 g. (48%) of pure rac[3aS-(3aβ,4α,6aβ)]-hexahydro-2-oxo-3-(phenylmethyl)-1H-thieno-[3,4-d]-imidazole-4-pentanoic acid methyl ester, m.p. 105°—106° C.

EXAMPLE 11

D,L-biotin methyl ester

A mixture of 0.30 g. (0.858 mmol) of rac[3aS-(3aβ,4'-,6aβ)]-hexahydro-2-oxo-3-(phenylmethyl)-1H-thieno-[3,4-d]-imidazole-4-pentanoic acid methyl ester and 10 ml. of 48% hydrobromic acid was refluxed for 3 hrs., then evaporated in vacuo to form crude d,l-biotin. This product was dissolved in 2 ml. of methanol and treated with a diazomethane solution in ether, until the yellow color persisted. The solvents were evaporated in vacuo and the residue crystallized from methylene chloride-ether to give 0.18 g. (81%) of d,l-biotin methyl ester, m.p. 136°-137° C.

We claim:

1. An optically active compound of the formula:

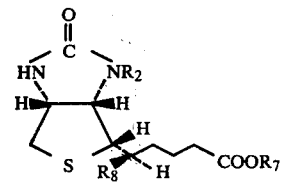

X'-XIII' wherein $R_2$ is benzyl or alpha-lower alkyl substituted benzyl, $R_7$ is hydrogen, lower alkyl, benzyl, alpha-lower alkyl substituted benzyl, alkali metal or alkaline earth metal; and $R_8$ is hydroxy or halide, or the racemate thereof.

2. The compound of claim 1 wherein $R_8$ is halide.

3. The compound of claim 2 wherein $R_7$ is hydrogen, lower alkyl, benzyl or alpha-lower alkyl substituted benzyl.

4. The compound of claim 3 wherein $R_2$ is benzyl, $R_7$ is methyl and $R_8$ is chloride.

5. The compound of claim 1 wherein $R_8$ is hydroxy.

6. The compound of claim 5 wherein $R_7$ is alkali metal or alkaline earth metal.

7. The compound of claim 6 wherein $R_2$ is benzyl and $R_7$ is sodium.

8. The compound of claim 5 wherein $R_7$ is hydrogen.

9. The compound of claim 8 wherein $R_2$ is benzyl.

* * * * *